US012496240B2

(12) United States Patent
Han et al.

(10) Patent No.: US 12,496,240 B2
(45) Date of Patent: Dec. 16, 2025

(54) AMBULANCE-TYPE MOBILE CATHETER ROOM FOR CARDIOVASCULAR INTERVENTIONAL SURGERY

(71) Applicant: GENERAL HOSPITAL OF PLA NORTHERN THEATER COMMAND, Shenyang (CN)

(72) Inventors: Yaling Han, Shenyang (CN); Jingyang Sun, Shenyang (CN); Ming Liang, Shenyang (CN); Xiaozeng Wang, Shenyang (CN); Yang Li, Shenyang (CN); Dan Liu, Shenyang (CN); Fei Li, Shenyang (CN)

(73) Assignee: GENERAL HOSPITAL OF PLA NORTHERN THEATER COMMAND, Shenyang (CN)

( * ) Notice: Subject to any disclaimer, the term of this patent is extended or adjusted under 35 U.S.C. 154(b) by 379 days.

(21) Appl. No.: 18/038,223

(22) PCT Filed: Mar. 31, 2021

(86) PCT No.: PCT/CN2021/084475
§ 371 (c)(1),
(2) Date: May 23, 2023

(87) PCT Pub. No.: WO2022/110597
PCT Pub. Date: Jun. 2, 2022

(65) Prior Publication Data

US 2024/0091082 A1 Mar. 21, 2024

(30) Foreign Application Priority Data

Nov. 24, 2020 (CN) ........................ 202011332604.8

(51) Int. Cl.
*A61G 3/00* (2006.01)
*A61B 34/37* (2016.01)
*A61B 6/00* (2006.01)

(52) U.S. Cl.
CPC .............. *A61G 3/001* (2013.01); *A61B 34/37* (2016.02); *A61B 6/4458* (2013.01); *A61B 6/4476* (2013.01)

(58) Field of Classification Search
CPC ........ A61G 3/001; A61G 3/008; A61G 10/00; A61G 10/005; A61G 10/02; A61B 6/4452;
(Continued)

(56) References Cited

U.S. PATENT DOCUMENTS 8,745,789 B2 * 6/2014 Saracen .................. B66C 23/48
5/601
10,207,728 B2 * 2/2019 Kaushansky ....... A61M 60/585
(Continued)

FOREIGN PATENT DOCUMENTS

CN 102949278 A 3/2013
CN 202843955 U 4/2013
(Continued)

OTHER PUBLICATIONS

English translation of CN206334026U; https://translationportal.epo.org; Jul. 30, 2025 (Year: 2025).*
(Continued)

*Primary Examiner* — Roger L Pang
(74) *Attorney, Agent, or Firm* — Bayramoglu Law Offices LLC

(57) ABSTRACT

An ambulance-type mobile catheter room for cardiovascular interventional surgery enables interventional diagnosis and treatment devices for acute and severe cardiovascular diseases to be deployed quickly, is flexible and high in adapt-
(Continued)

ability, and provides hardware devices for cardiovascular diagnosis and treatment interventional surgeons to timely diagnose and treat patients. The ambulance-type mobile catheter room for cardiovascular interventional surgery includes an ambulance. The ambulance is internally provided with an antibacterial internal environment, a robotic angiography machine system, a wireless medical Internet of Things system, a self-generating system and an auxiliary system.

9 Claims, 15 Drawing Sheets

(58) Field of Classification Search
CPC . A61B 6/547; A61B 2090/376; A61B 6/0407; A61B 6/587; A61B 6/4458; A61B 6/0487; A61B 6/4476
USPC .................. 296/19, 24.38; 378/62, 196, 197
See application file for complete search history.

(56) References Cited

U.S. PATENT DOCUMENTS

| | | | | |
|---|---|---|---|---|
| 2013/0223597 | A1* | 8/2013 | Graumann | A61B 6/4476 378/197 |
| 2017/0259764 | A1* | 9/2017 | Da Silva Carvalho | B60L 8/003 |
| 2018/0242938 | A1 | 8/2018 | Tanaka et al. | |
| 2021/0187271 | A1* | 6/2021 | Mele | A61M 60/497 |
| 2021/0315748 | A1* | 10/2021 | Hamilton | A61G 3/001 |
| 2023/0404497 | A1* | 12/2023 | Han | A61B 6/4405 |

FOREIGN PATENT DOCUMENTS

| | | | | |
|---|---|---|---|---|
| CN | 103239330 | A | 8/2013 | |
| CN | 103831821 | A | 6/2014 | |
| CN | 203693571 | U | 7/2014 | |
| CN | 105358062 | A | 2/2016 | |
| CN | 206334026 | U | 7/2017 | |
| CN | 108095748 | A | 6/2018 | |
| CN | 110090036 | A | 8/2019 | |
| CN | 209713431 | U | 12/2019 | |
| CN | 111317496 | A | 6/2020 | |
| CN | 112386407 | A | 2/2021 | |
| DE | 102008035195 | A1 | 2/2010 | |
| EP | 2446870 | A2 * | 5/2012 | A61G 3/001 |
| JP | 2001299743 | A | 10/2001 | |
| KR | 20160092424 | A | 8/2016 | |

OTHER PUBLICATIONS

English translation of CN203693571U; https://translationportal.epo.org; Jul. 30, 2025 (Year: 2025).*
English translation of CN108095748A; https://translationportal.epo.org; Jul. 30, 2025 (Year: 2025).*
CN109498291A with English translation; Li; Mar. 22, 2019 (Year: 2025).*

* cited by examiner

AMBULANCE-TYPE MOBILE CATHETER ROOM FOR CARDIOVASCULAR INTERVENTIONAL SURGERY

CROSS REFERENCE TO THE RELATED APPLICATIONS

This application is the national phase entry of International Application No. PCT/CN2021/084475, filed on Mar. 31, 2021, which is based upon and claims priority to Chinese Patent Application No. 202011332604.8, filed on Nov. 24, 2020, the entire contents of which are incorporated herein by reference.

TECHNICAL FIELD

The present invention relates to a mobile catheter room, and more particularly relates to an ambulance-type mobile catheter room for cardiovascular interventional surgery.

BACKGROUND

At present, the most effective mode for the treatment of acute myocardial infarction is to adopt a percutaneous coronary intervention method to quickly open infarction-related coronary arteries, however, percutaneous coronary intervention needs to be performed under the conditions of an interventional catheter room equipped with related interventional devices such as a cardiovascular angiography X-ray machine. At present, an existing diagnosis and treatment mode for the treatment of acute myocardial infarction at home and abroad is to transfer patients to hospitals with a vascular intervention catheter room for vascular intervention to open blood vessels. However, statistics show that about 50% of acute myocardial infarction patients die on the way. At present, although a studied vehicle-mounted mobile shelter with the function of interventional catheter room can deliver the devices and interventional surgeons to the patient diagnosis and treatment site, due to the large volume of a shelter system, the large deployment area before the surgery, the long deployment time and the long folding time after the surgery, and unavailable "immediate" surgical rescue according to the patient condition during transportation, this kind of interventional surgery shelter cannot realize timely diagnosis and treatment for acute myocardial infarction patients in random areas.

A kind of miniaturized cardiovascular interventional catheter room with good mobility, high integration, strong maneuverability and fast response speed is urgently needed, which can quickly arrive at the site where patients suffer from acute myocardial infarction, can be rapidly deployed on the site to "immediately" carry out minimally invasive interventional surgery diagnosis and treatment for the patients, and at the same time, has the function of performing interventional surgery at any time according to the conditions on the way to the hospital to ensure vital signs of the patients.

SUMMARY

The present invention provides, specific to defects in the prior art, an ambulance-type mobile catheter room for cardiovascular interventional surgery, which is a rapid minimally invasive interventional diagnosis and treatment shelter for acute and severe heart and vascular diseases for field operations, enables interventional diagnosis and treatment devices for acute and severe cardiovascular diseases to be deployed quickly, is flexible and high in adaptability, and provides hardware devices for cardiovascular diagnosis and treatment interventional surgeons to timely diagnose and treat patients.

For achieving the above objective, the present invention adopts a following technical solution, in which an ambulance is included and internally provided with an antibacterial internal environment, a robotic angiography machine system, a wireless medical Internet of Things system, a self-generating system and an auxiliary system.

Further, the ambulance includes a chassis and a compartment, and the chassis is a long-axis chassis used for assembling a (high-power) engine and the self-generating system; and the compartment is movably connected to the chassis.

Further, lead plates are sandwiched between the outer wall of the compartment and the interior, and compartment windows, the compartment body and cab windows all adopt lead glass.

Further, the compartment is internally equipped with an instrument container, an apparatus container and an apparatus trolley, and the compartment is internally equipped with a laminar flow apparatus, a purification air conditioner, a fan heater, an oxygen supply system, a water supply system, and a video transmission device.

Further, the robotic angiography machine system consists of a robotic upper arm (an upper robotic arm type robot), a robotic lower arm (a lower robotic arm type robot), a robot controller and an image chain system.

Further, both the upper robotic arm type robot and the lower robotic arm type robot adopt robotic arms of seven degrees of freedom, a tail end of the upper robotic arm type robot is connected to a ball tube, a tail end of the lower robotic arm type robot is connected to a flat panel detector, the upper robotic arm type robot is fixed to a compartment top, and the lower robotic arm type robot is fixed to a compartment bottom.

Further, the robot controller realizes the adjustment and calibration of robot end centering according to image data of an X-ray on the flat panel detector.

Further, the image chain system includes the ball tube, the flat panel detector, a high-voltage generator, a medical display and a workstation, where software control of the high-voltage generator, the medical display and the workstation is matched with the robot controller for application.

Further, the auxiliary system includes an emergency stretcher/interventional comprehensive table, an electrocardiograph, a handheld ultrasound device, a defibrillator-monitor, an invasive blood pressure monitor and a vehicle-mounted intra-aortic balloon pump (IABP).

Further, the self-generating system includes a generator apparatus and a gearbox; and the generator apparatus includes belt power takeoff driving, and the gearbox includes a parking generator apparatus.

Further, the antibacterial internal environment includes laminar flow purification (device), ultraviolet sterilization lamps and an antibacterial material inner wall.

Further, the wireless medical Internet of Things system includes a medical data acquisition terminal, a camera inside the compartment and a medical monitoring device, and wireless remote data interaction is realized after the audio and video of the physical scene in the compartment and medical device monitoring information are collected by the data acquisition terminal.

Compared with the prior art, the present invention has the following beneficial effects.

In order to overall bring ahead a cardiovascular system acute and severe injury diagnosis and treatment gateway, the present invention provides a rapid minimally invasive interventional diagnosis and treatment shelter for cardiovascular acute and severe injuries in the field, which enables interventional diagnosis and treatment devices for acute and severe cardiovascular diseases to be deployed quickly, is flexible and high in adaptability, and provides hardware devices for timely diagnosis and treatment on patients by cardiovascular diagnosis and treatment interventional surgeons.

BRIEF DESCRIPTION OF THE DRAWINGS

The present invention is further described below with reference to the accompanying drawings and specific implementations. The scope of protection of the present invention is not limited to the expression of the following content.

In the figures, 1—robotic upper arm, 2—robotic lower arm, 3—operating table, 4—folding table, 5—hand sanitizer box, 6—image chain system, 7—folding single seat, 8—wall cabinet, 9—device fixing module, 10—mobile spotlight, 11—lighting belt, 12—infusion hook, 13—signal port, 14—power port, 15—boarding pedal, 16—partition wall, 17—electric winch, 18—blue rotational type police light siren, 19—air conditioner, 20—slim police light, 21—red cross logo, 22—rear door spare tire, 23—electric wash basin, 24—water tank, 25—power supply system, 26—laminar flow purification device, 27—medicine box, 28—storage battery, and 29—oxygen cylinder.

DETAILED DESCRIPTION OF THE EMBODIMENTS

Figure 1:
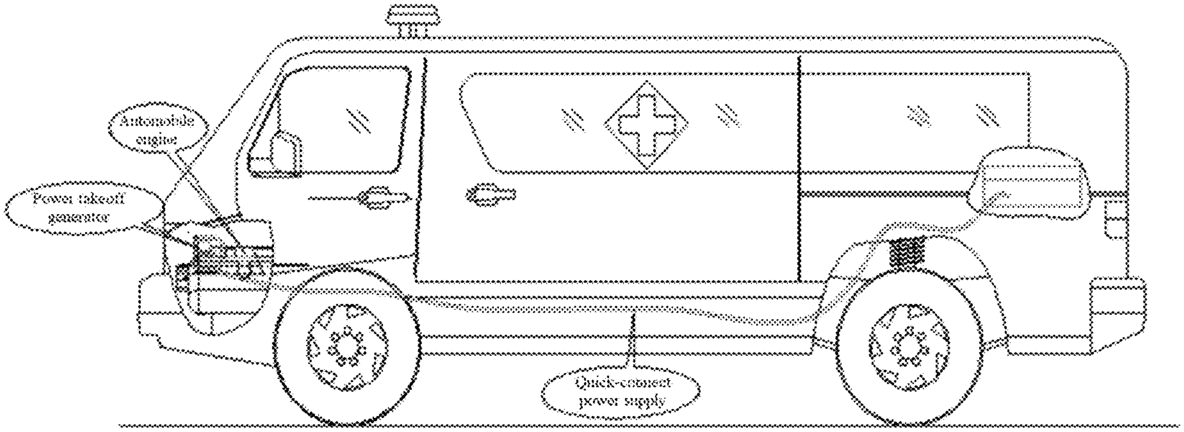
FIG. 1 is an overall schematic structural diagram according to the present invention.
Figure 2:
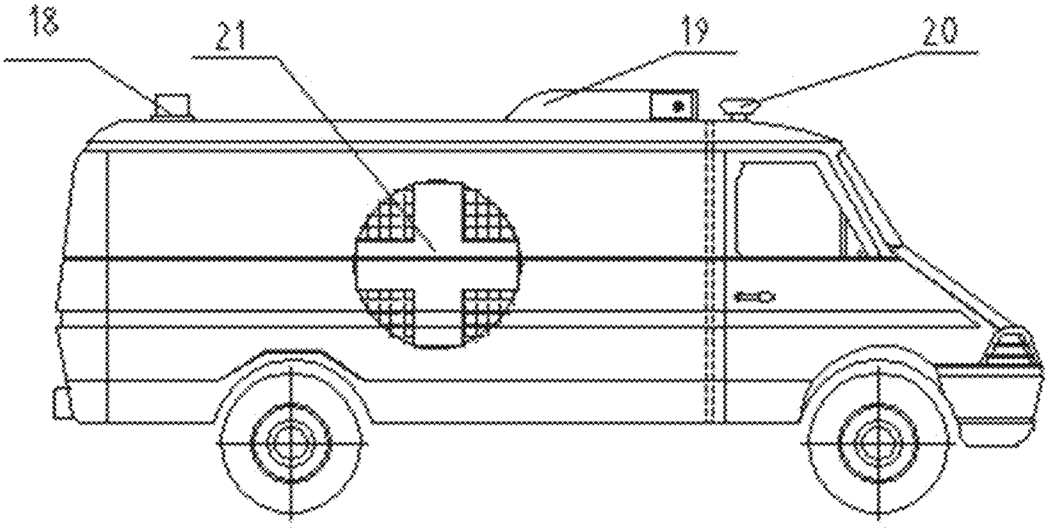
FIGS. 2 to 3 are whole ambulance external arrangement diagrams according to the present invention.
Figure 3:
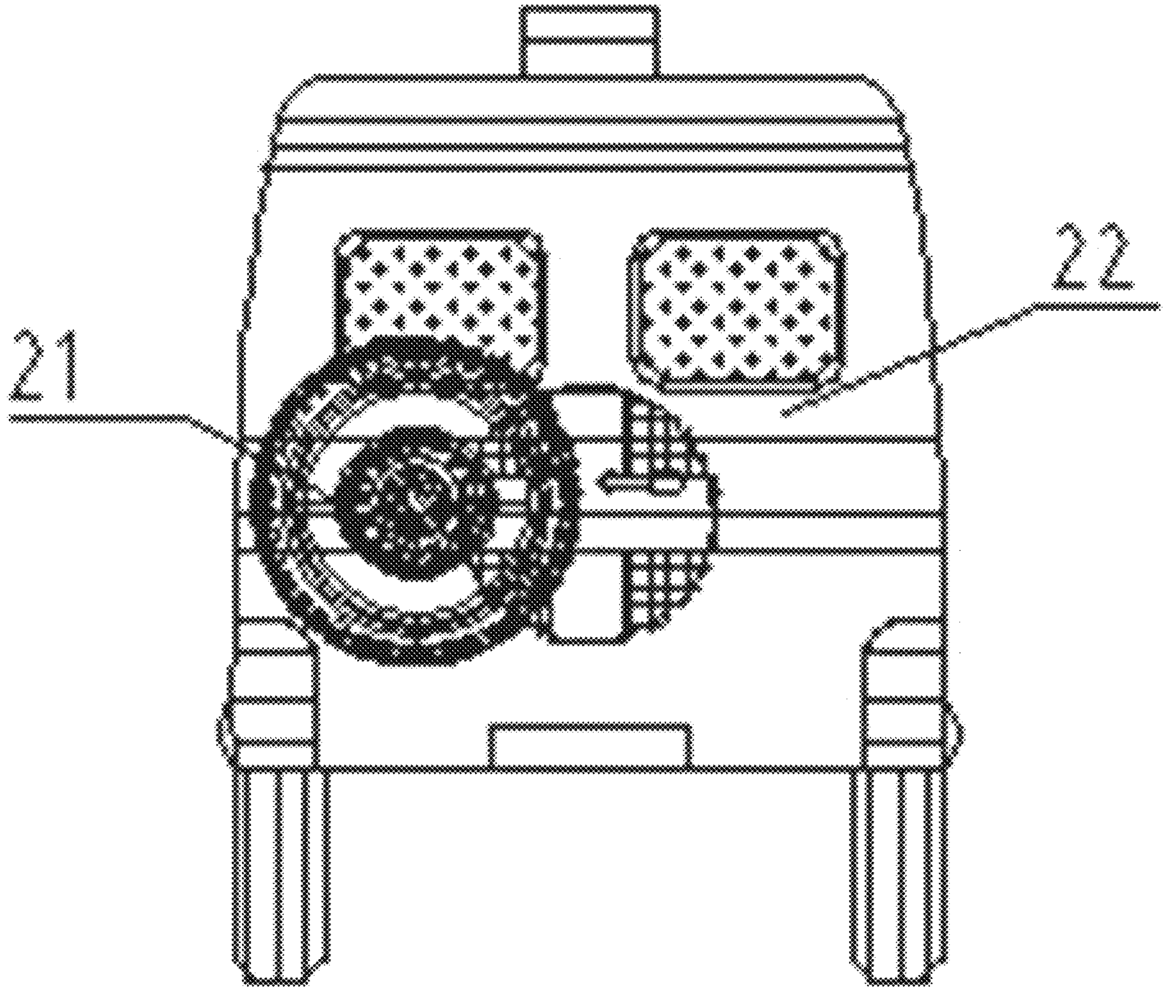
Figure 4:
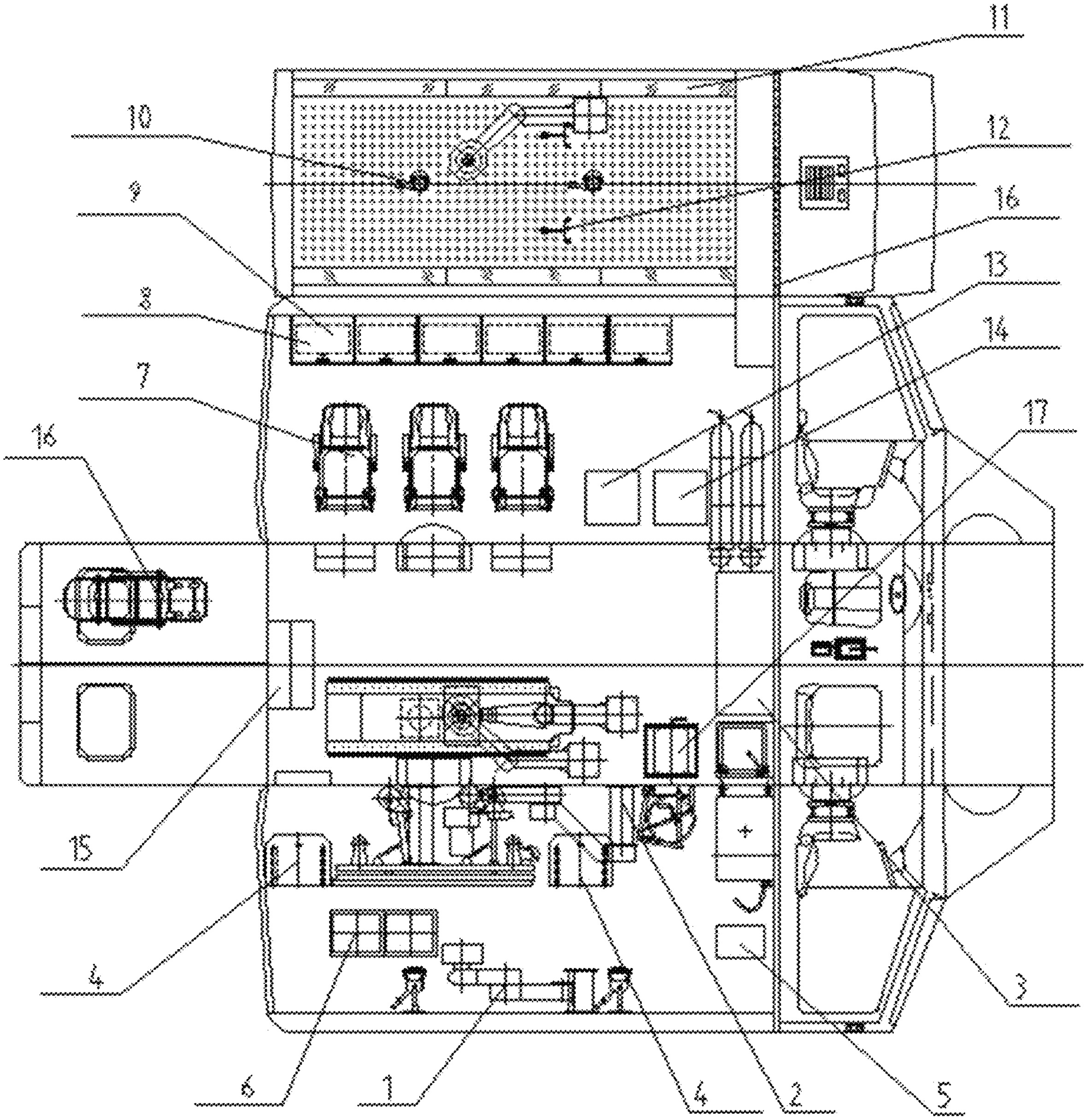
FIGS. 4 to 5 are interior arrangement diagrams of a compartment according to the present invention.
Figure 5:
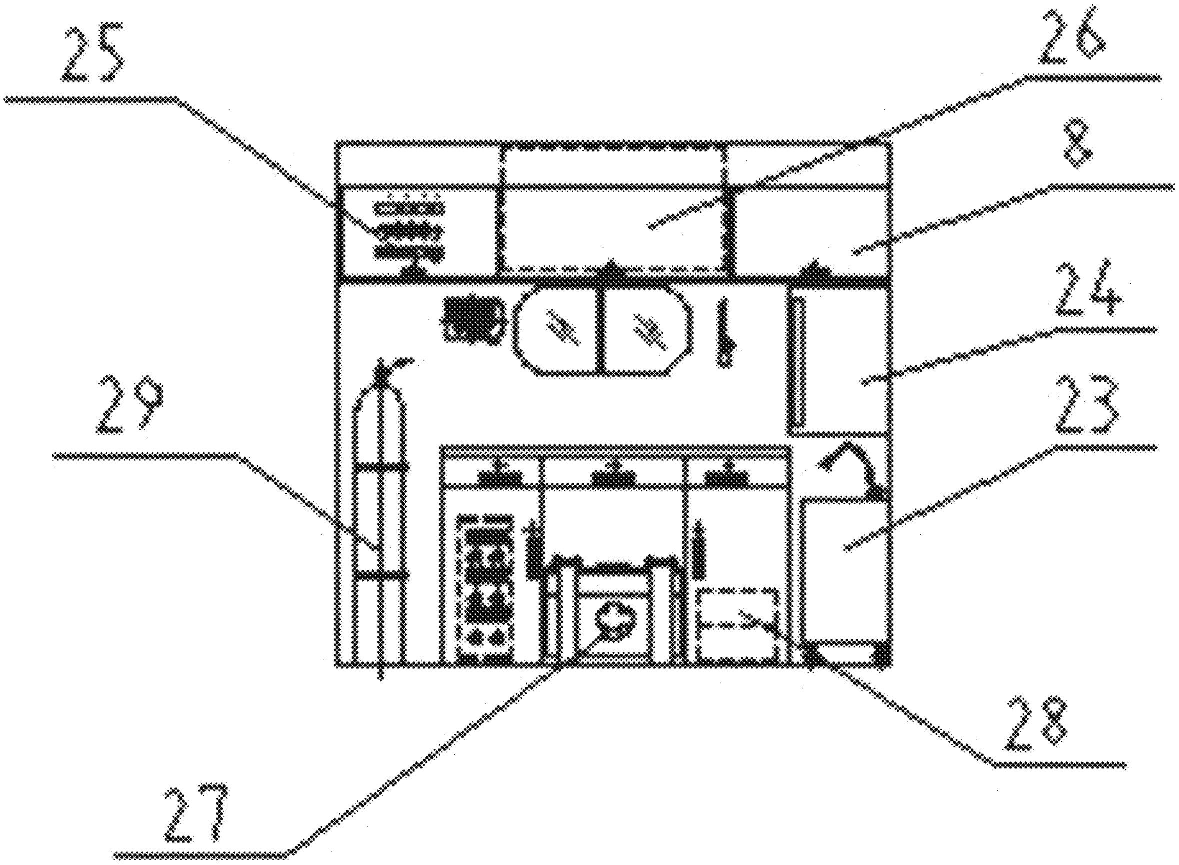
Figure 6A:
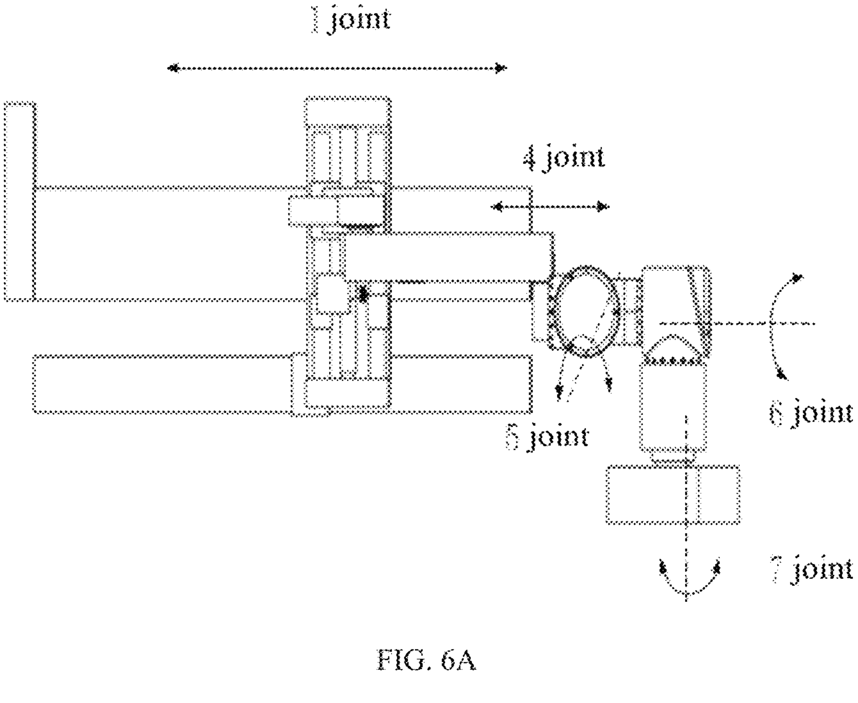
FIGS. 6A to 6B are schematic diagrams of a robotic upper arm joint structure according to the present invention.
Figure 6B:
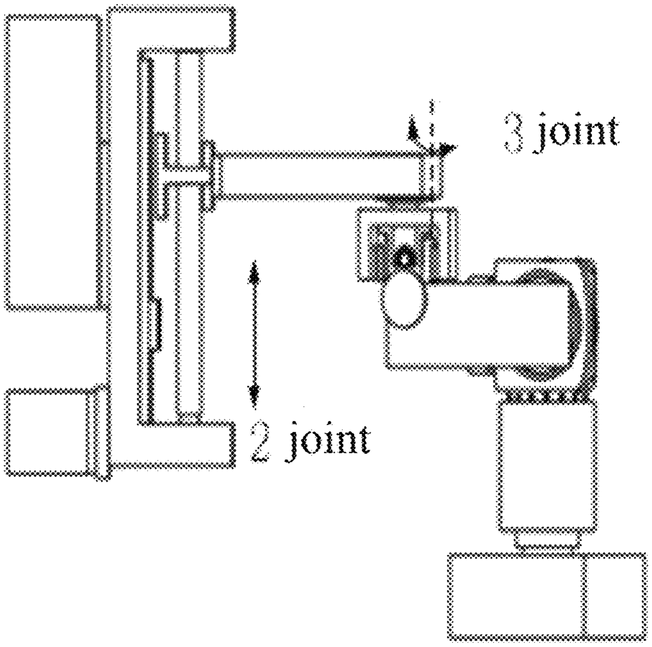
Figure 7A:
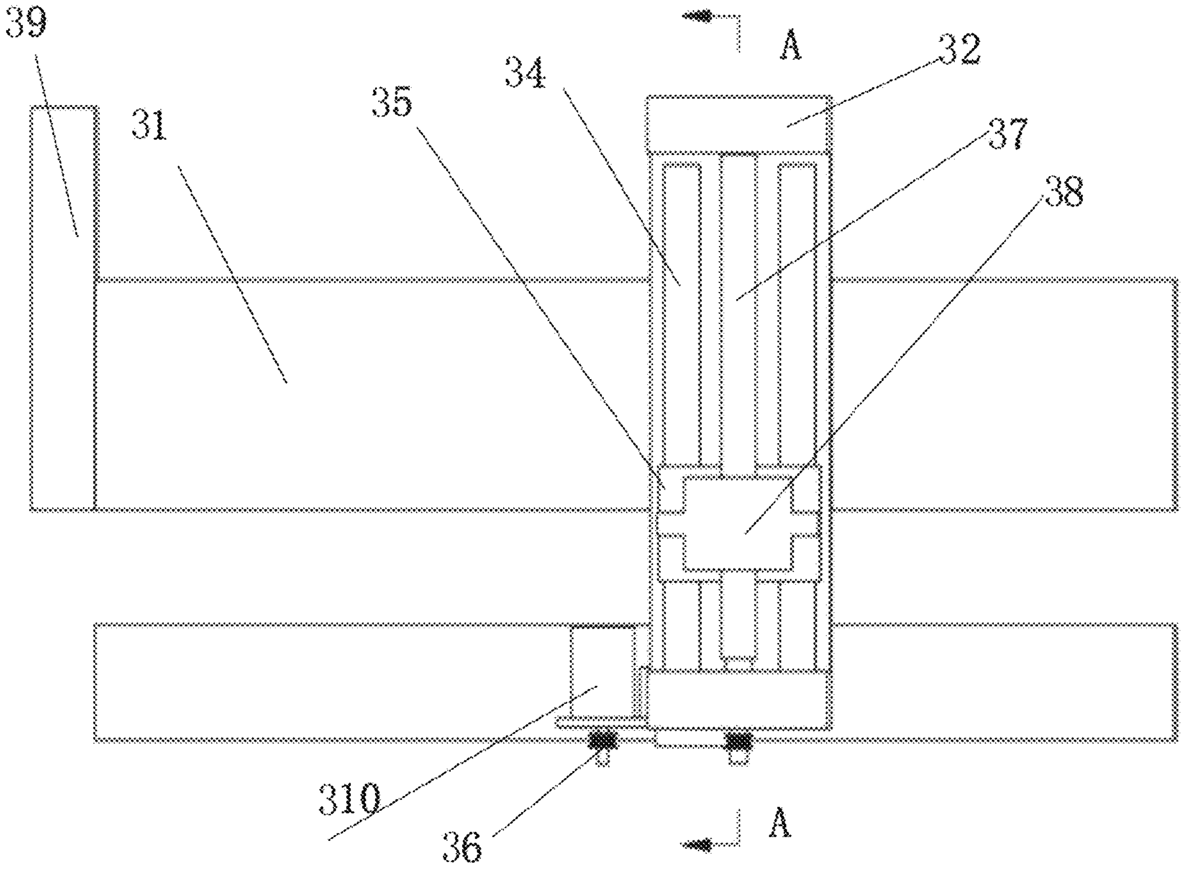
FIGS. 7A to 7B are schematic diagrams of an upper arm first-second joint structure according to the present invention.
Figure 7B:
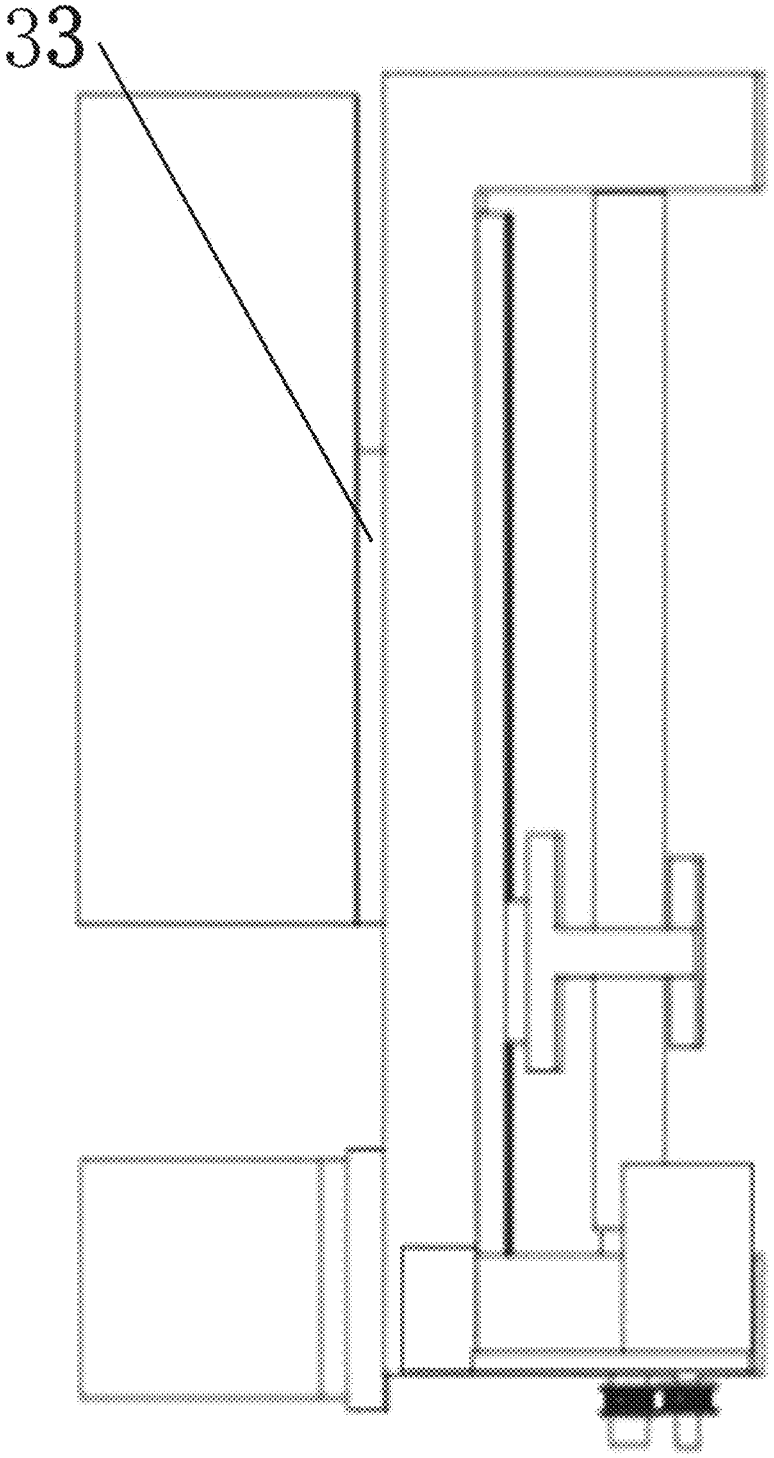
Figure 7C:
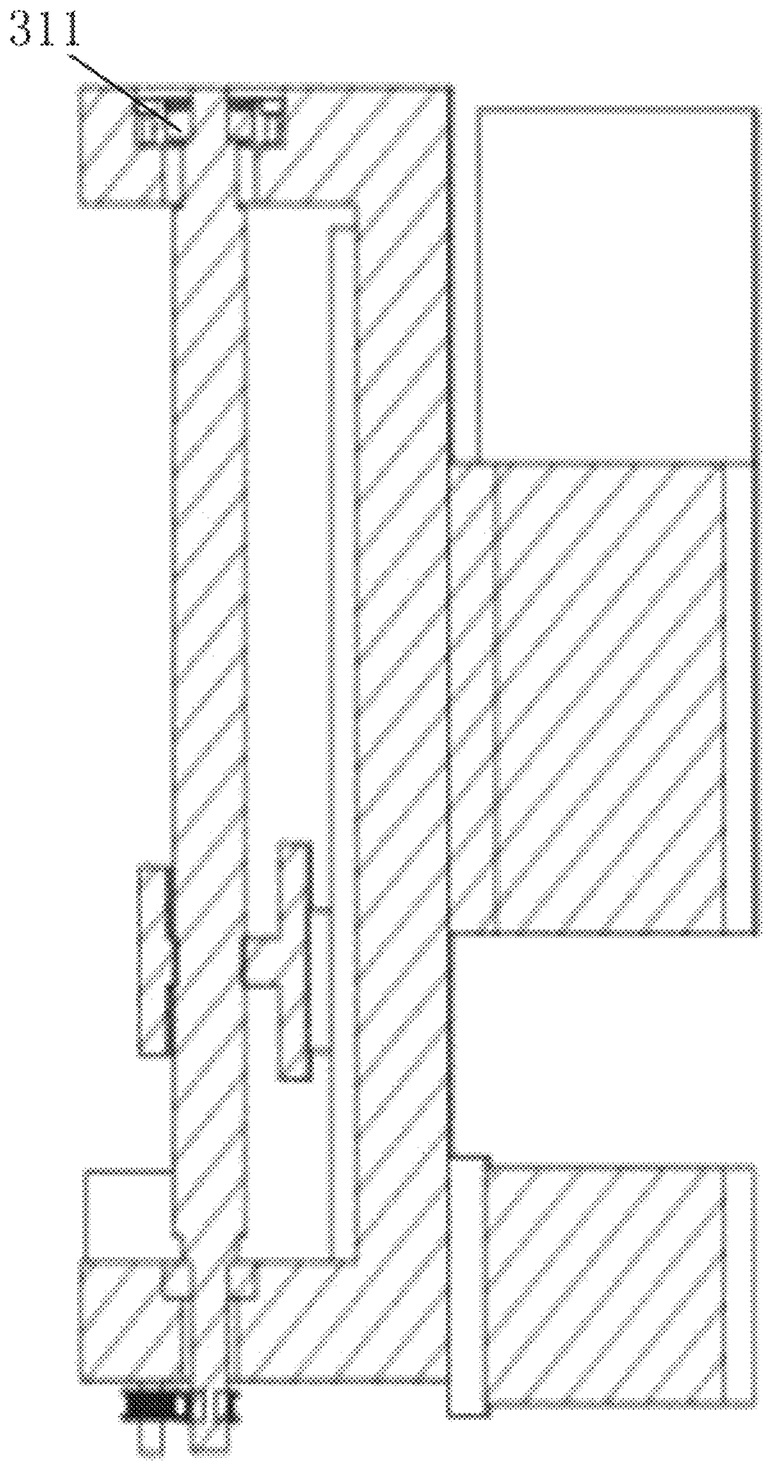
FIG. 7C is a schematic diagram of A-A in FIG. 7A according to the present invention.
Figure 8:
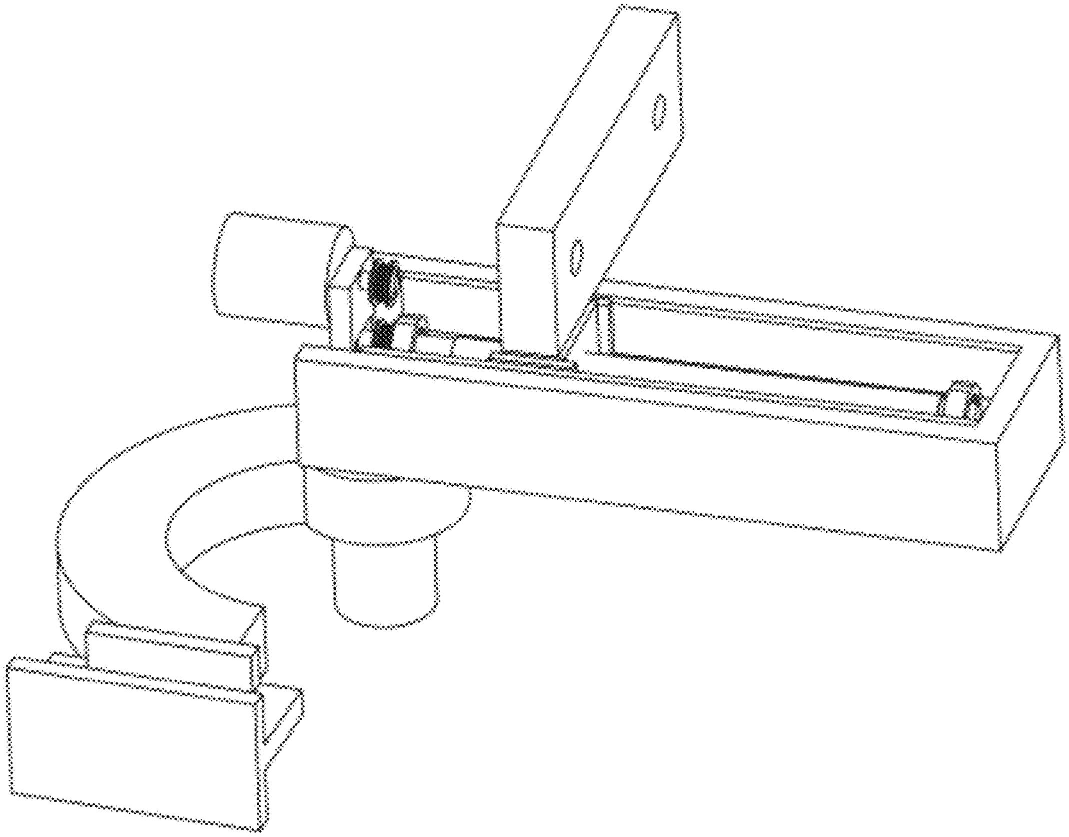
FIG. 8 is a connection schematic diagram of an upper arm third joint and an upper arm fourth joint according to the present invention.
Figure 9:
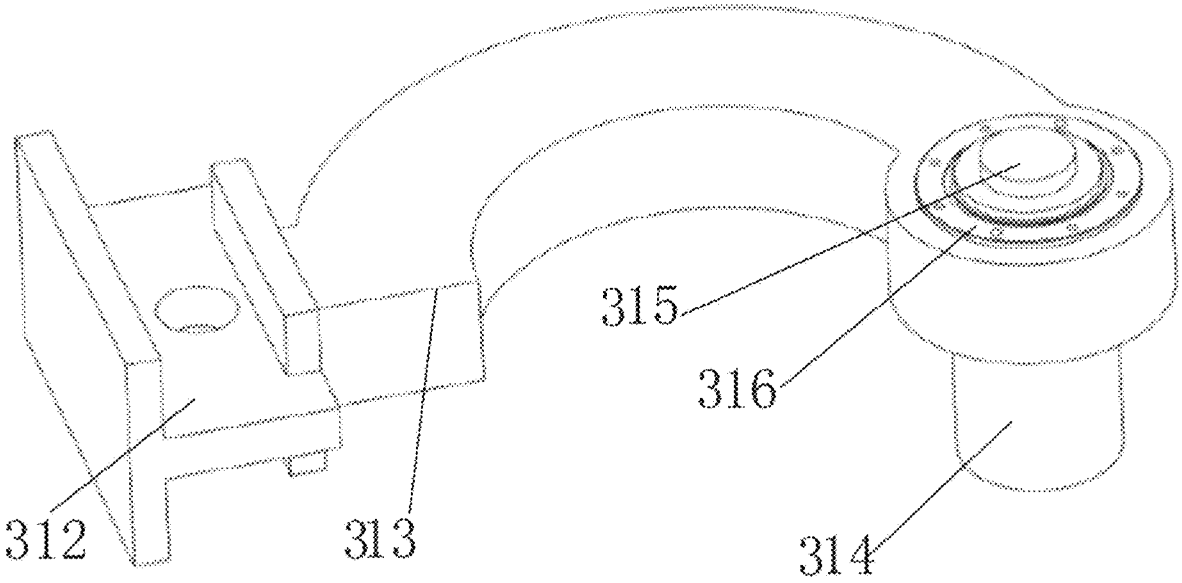
FIG. 9 is a connection schematic diagram of an upper arm third joint according to the present invention.
Figure 10:
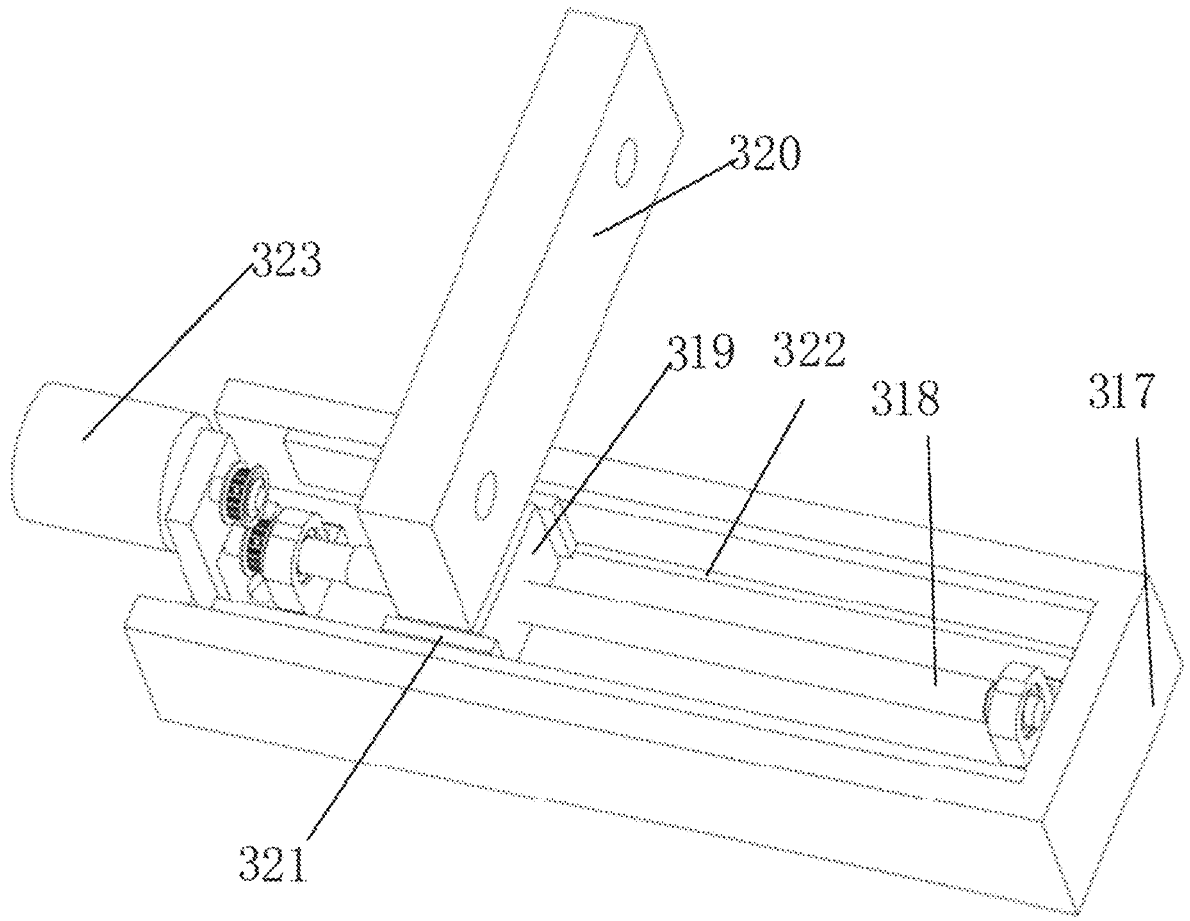
FIG. 10 is a connection schematic diagram of an upper arm fourth joint according to the present invention.
Figure 11A:
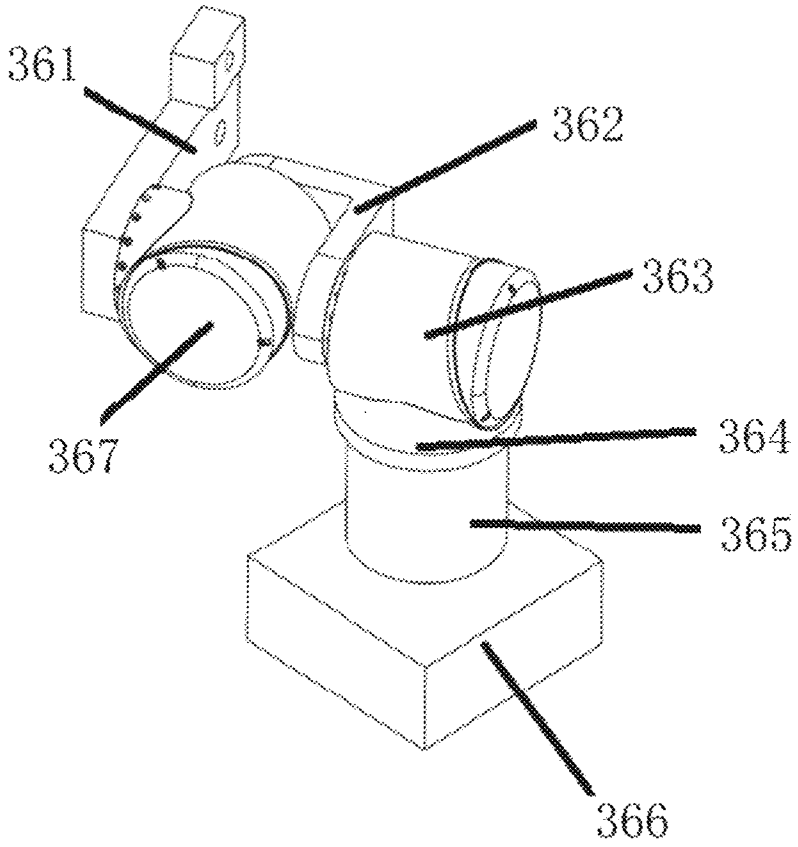
FIGS. 11A to 11B are schematic diagrams of a 5-6-7 joint structure.
Figure 11B:
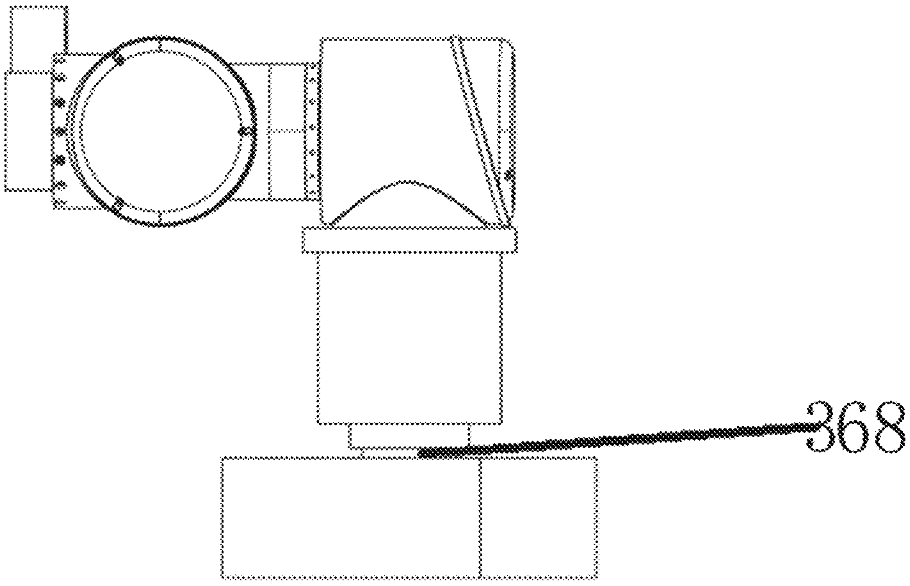
Figure 12A:
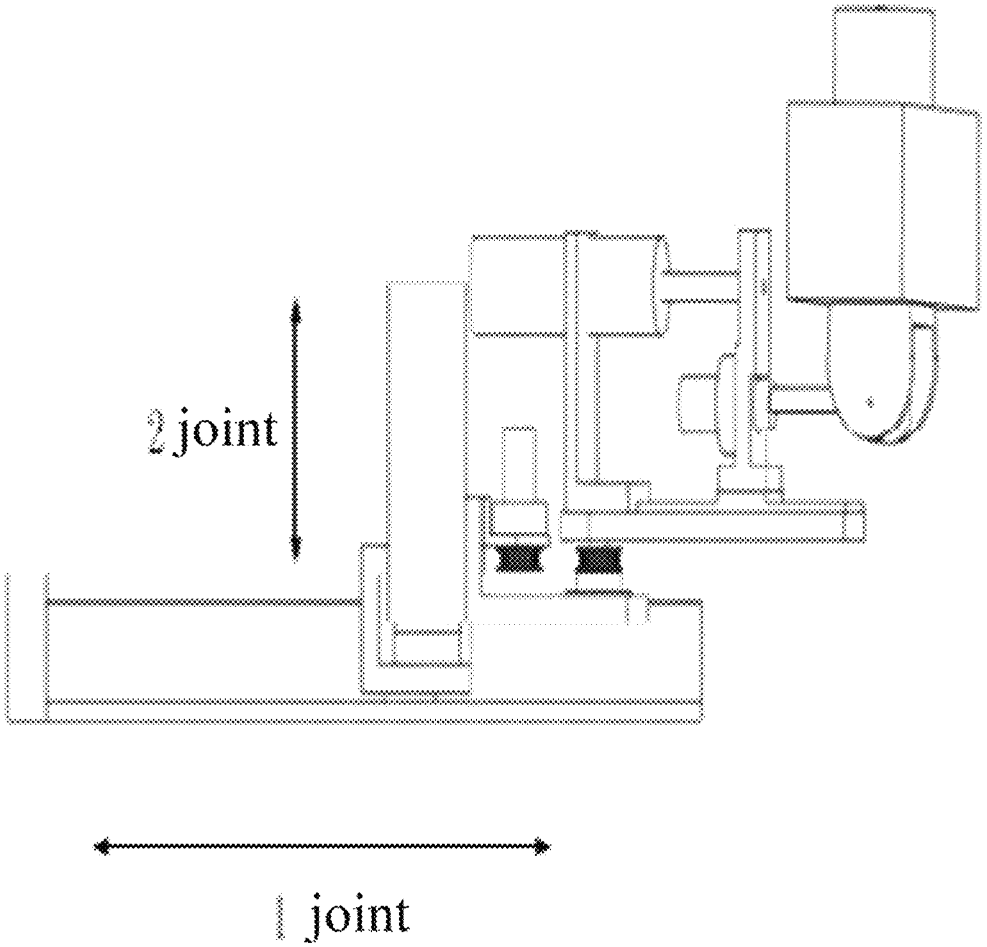
FIGS. 12A to 12B are schematic diagrams of a robotic lower arm joint structure according to the present invention.
Figure 12B:
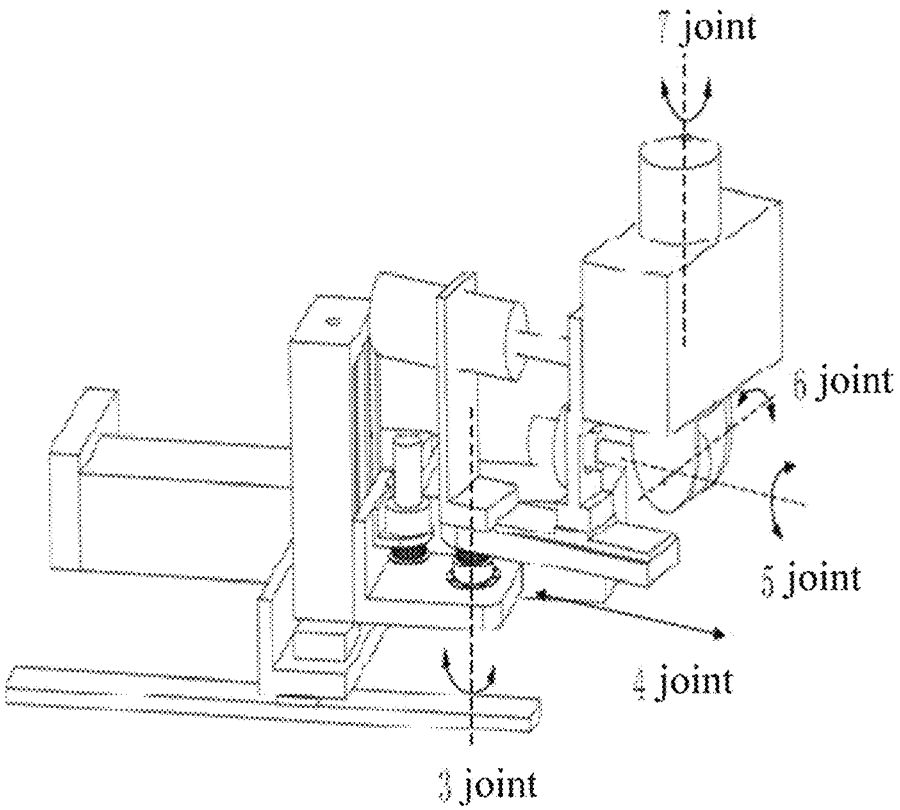
Figure 13:
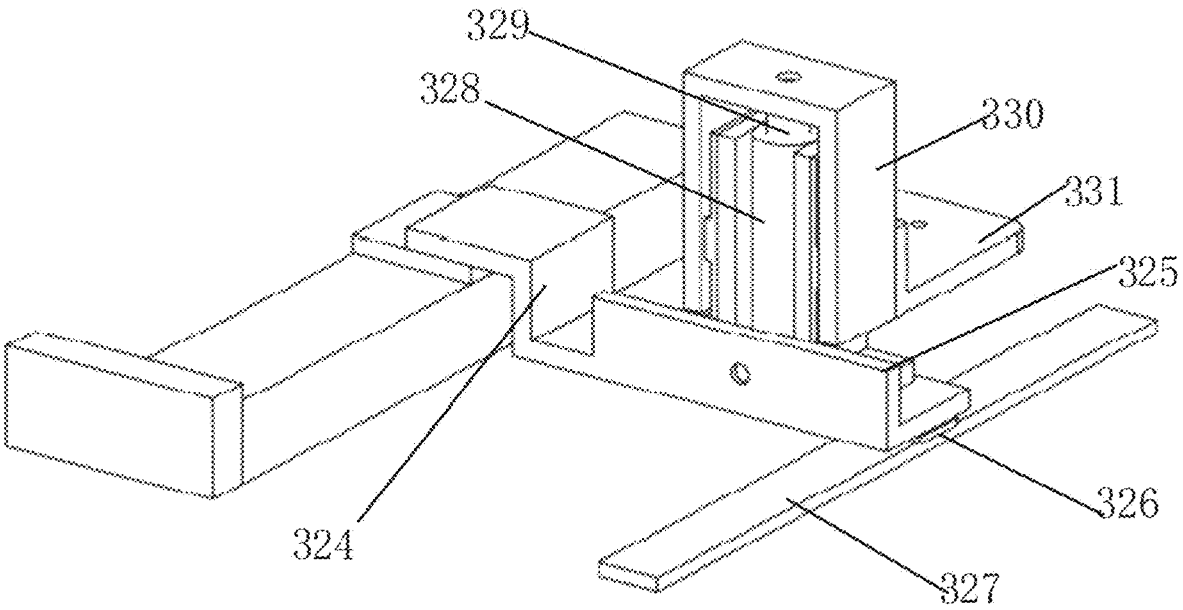
FIG. 13 is a schematic diagram of a lower arm first-second joint according to the present invention.
Figure 14:
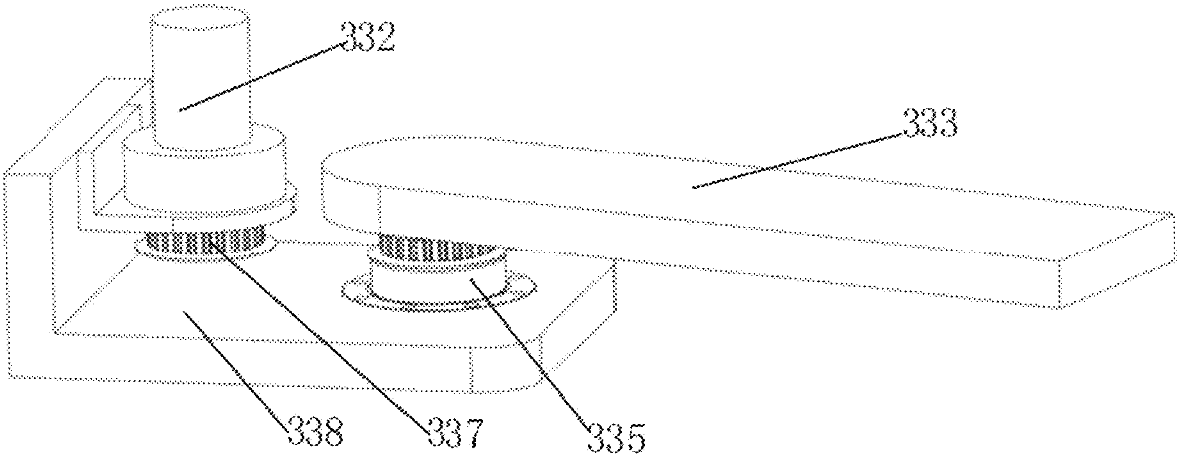
FIG. 14 is a schematic diagram of a lower arm third joint according to the present invention.
Figure 15A:
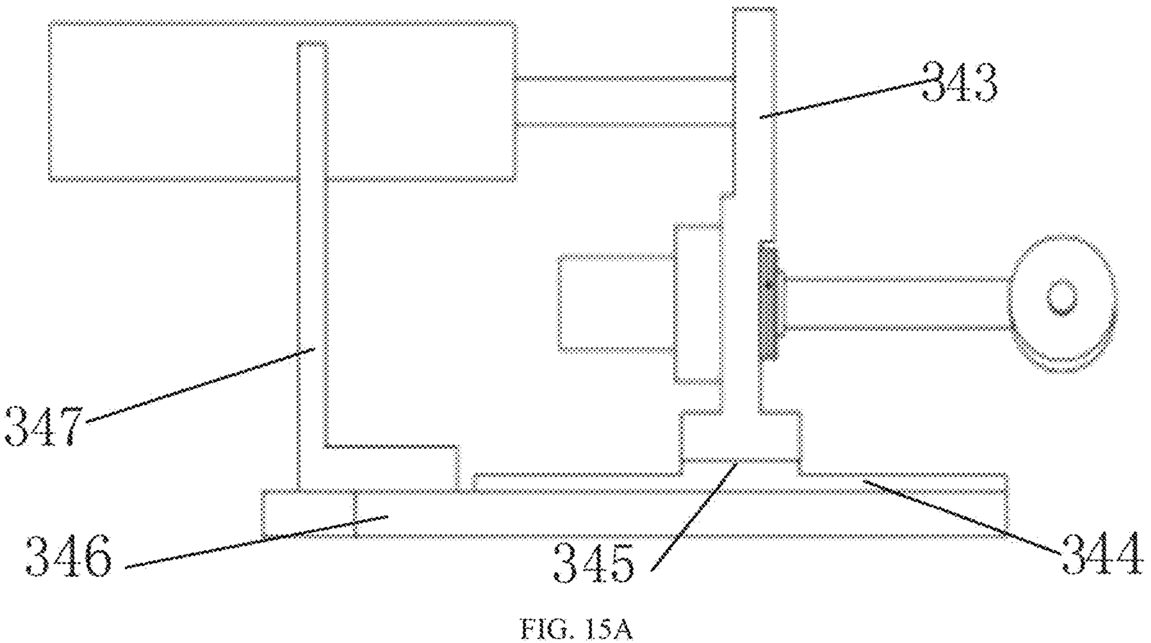
FIGS. 15A to 15B are schematic diagrams of a lower-arm fourth and fifth joint according to the present invention.
Figure 15B:
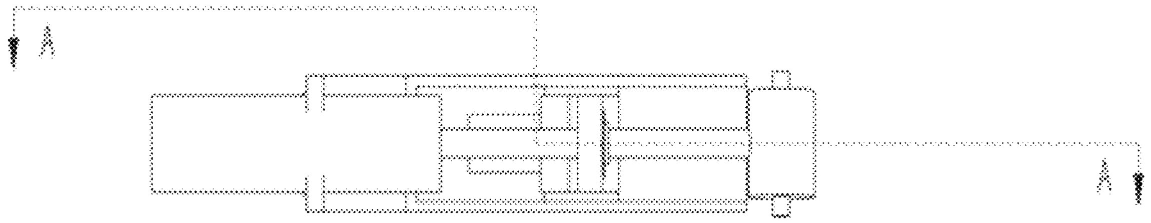
Figure 15C:
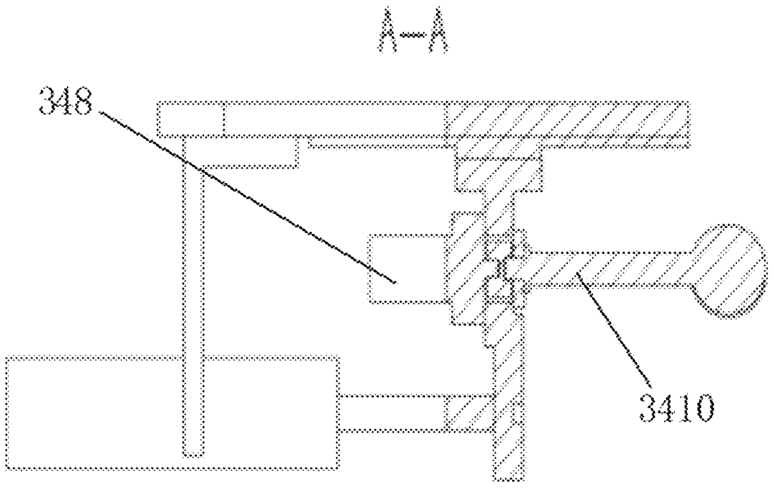
FIG. 15C is a schematic diagram of A-A in FIG. 15B.
Figure 16A:
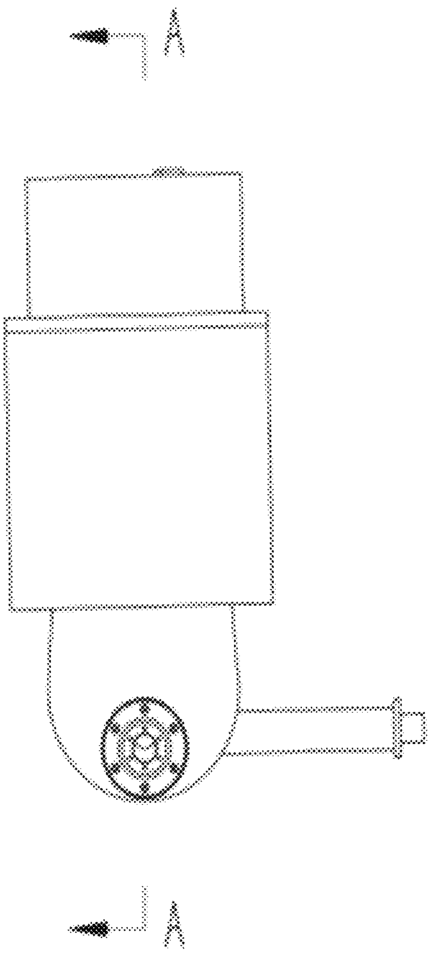
FIG. 16A is a schematic diagram of a lower-arm sixth and seventh joint structure.
Figure 16B:
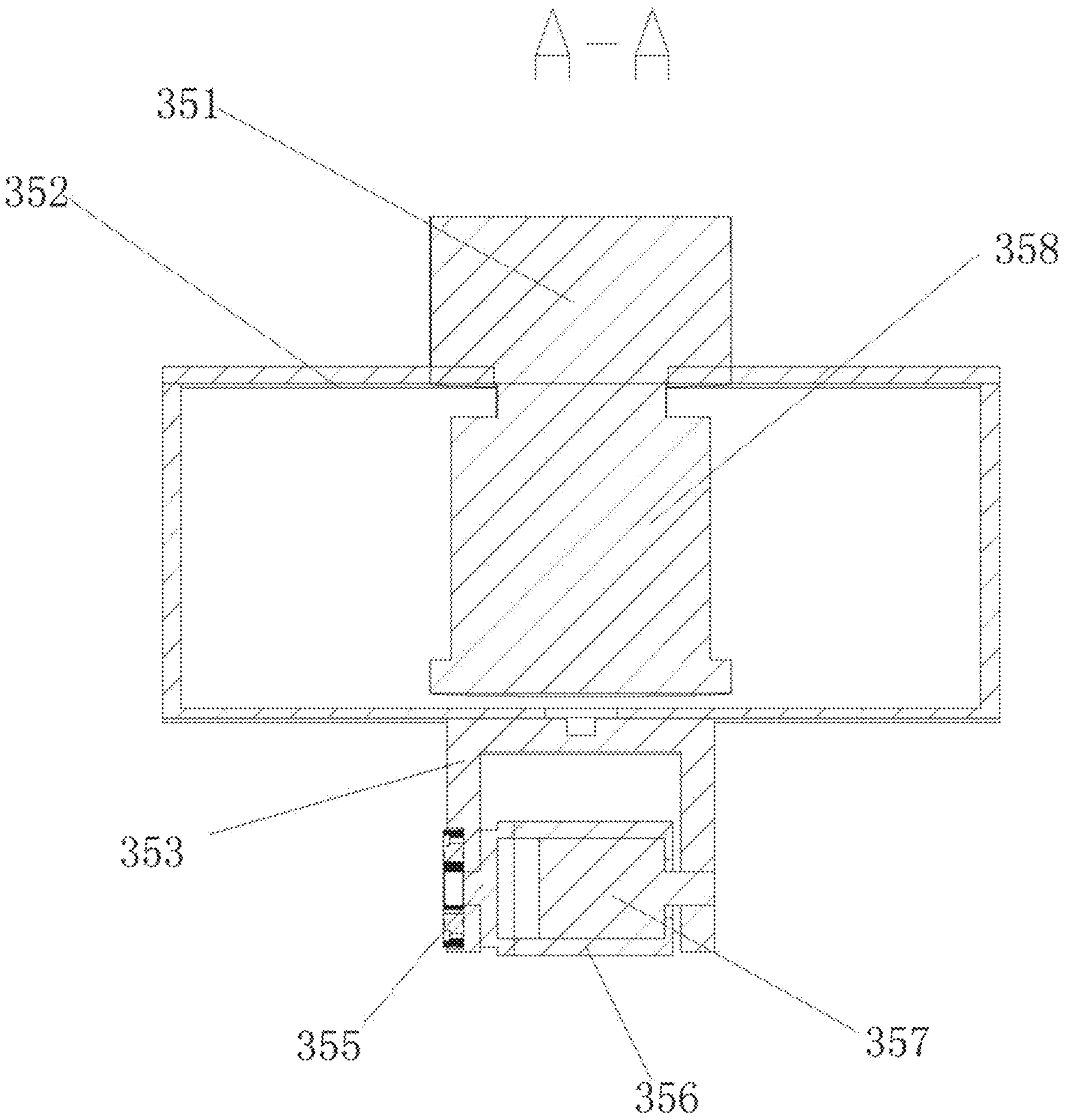
FIG. 16B is a schematic diagram of A-A in FIG. 16A.

As shown in FIGS. 1 to 16B, as a kind of specific embodiment: the present invention includes an ambulance, a robotic angiography machine system, an auxiliary device system, a self-generating system, a wireless medical Internet of Things system, an antibacterial internal environment, etc.

The ambulance has an operating table, a folding table, a hand sanitizer box, an image chain system, folding single seats, a wall cabinet, mobile spotlights, a lighting belt, infusion hooks, a signal port, a power port, a boarding pedal, a stair stretcher, a partition wall, an electric winch, an electric wash basin, a water tank, a power supply system, a laminar flow purification device, a medicine box, a storage battery, an inverter power supply, and an oxygen cylinder.

The wall cabinet is used to accommodate device fixing modules.

A blue rotational type police light siren, an air conditioner, a slim police light, a red cross logo, a rear door spare tire, a rear double door are arranged outside the ambulance.

In the embodiment, the ambulance includes a chassis and a compartment, and the chassis is a long-axis chassis equipped with a high-power engine and the self-generating system. The compartment and the chassis are movably and adjustably connected.

In the embodiment, an electric telescopic support balance system is arranged around the bottom of the compartment. Lead plates are sandwiched between the outer wall of the compartment and the interior, and surrounding windows and a partition between the compartment body and the cab are equipped with lead glass.

In the embodiment, the compartment body is internally equipped with auxiliary devices such as an instrument container, an apparatus container and an apparatus trolley. The compartment is internally equipped with a laminar flow apparatus, a purification air conditioner, a fan heater, an oxygen supply system, a water supply system, a video transmission device, etc.

In the embodiment, the robotic angiography machine system consists of upper-lower robotic arm type double robots, a controller and the image chain system.

In the embodiment, the upper and lower robots are robotic arms of seven degrees of freedom (a robotic upper arm and a robotic lower arm), the end portions respectively fix a ball tube and a flat panel detector, the root portions are respectively fixed to the compartment top and the compartment bottom, and motion postures thereof are all centered.

The end portion of the upper arm is connected to the flat panel detector of an angiography machine, and the end portion of the lower arm is connected to the anode ball tube of the angiography machine. Through the motion of the upper arm and the lower arm, the isocenter detection in a wide range, different angles, and different isocenter distances can be realized, and high-quality angiograms can be provided for minimally invasive surgery.

In the embodiment, both the robotic upper arm and the robotic lower arm have seven degrees of freedom, including seven-degree-of-freedom modules.

In the embodiment, the seven-degree-of-freedom module of the upper arm includes a first-second joint linear motion module, a third-fourth joint module, and a fifth-sixth-seventh joint module.

In the embodiment, the first-second joint linear motion module of the seven-degree-of-freedom module of the upper arm includes a first-shaft joint linear module 31, and a second-shaft base 32 arranged on the first-shaft joint linear module 31; a first-shaft joint linear module output end 33 drives the second-shaft base 32 to move, the second-shaft base 32 is provided with second-shaft guide rails 34, the second-shaft guide rails 34 are slidably connected with a second-shaft slide block 35, the second-shaft slide block 35 transmits force to a screw nut pair through second-shaft pulleys 36, and the second-shaft pulleys 36 adopt a synchronous belt structure, and the synchronous belt structure is driven by a second-shaft motor 310; and two ends of a second-shaft screw 37 are supported, by second-shaft thrust bearings 311, on the second-shaft base 32, a second-shaft nut 38 is connected to the second-shaft slide block 35. Among them, the first-shaft joint linear module adopts a first-shaft guide rail, and a first-shaft slide block slidably connected to the first-shaft guide rail, which is realized under driving of a first-shaft motor 39, and it will not be repeated herein.

Specifically, an internal structure form of a first joint is similar to that of a second joint, which is not repeated. The first joint drives the second-shaft base to move through the first-shaft linear module output end, while the first-shaft guide rail plays a supporting role; the second joint mainly transmits, by the pulleys, force to the screw nut pair, two sides of a screw are supported by the thrust bearings, and the nut is connected to the two guide rail slide blocks (playing a supporting role) to output the motion to a next shaft.

In the embodiment, the second-shaft guide rails 34 include a first second-shaft guide rail and a second second-shaft guide rail arranged in parallel.

In the embodiment, the third-fourth joint module of the seven-degree-of-freedom module of the upper arm includes a third joint module, and a fourth-joint module; and the third joint module includes a second-shaft connection block 312 fixed to the second-shaft slide block 35, one side of the second-shaft connection block 312 is connected with a curved arm type third-shaft connecting rod 313, the bottom of a free end of the third-shaft connecting rod 313 is provided with a third-shaft motor 314, the top of the free end is provided with a third-shaft motor connector 315, and the third-shaft motor connector 315 is connected to the free end through a third-shaft crossed roller bearing 316, an outer ring of the third-shaft crossed roller bearing 316 is connected to the free end, an inner ring of the third-shaft crossed roller bearing 316 is connected to a third-shaft motor 314 adapter, and the third-shaft motor 314 is connected to the third-shaft motor adapter 315 to transmit the motion to the third-shaft motor adapter 315.

The fourth joint module includes a fourth-joint base 317 fixedly connected to the third-shaft motor adapter 315, and the fourth-joint base 317 is internally equipped with a fourth-joint screw 318, and the fourth-joint screw 318 is installed in the base 316 through a bearing seat, and the screw 318 is connected to a fourth-joint nut 319 to form a screw nut kinematic pair, the nut 319 is connected to a block fourth-shaft connector 320, and the fourth-joint nut 319 is connected to fourth-joint slide blocks 321, the fourth-joint slide blocks 321 are connected to fourth-joint guide rails 322, and the fourth-joint guide rails 322 are arranged in the base and are parallel with the fourth-joint screw; and the fourth-joint screw transmits, by pulleys, force to the screw nut kinematic pair. Where a synchronous belt transmission mechanism is adopted in pulley transmission and adopts a fourth-shaft motor 323 as a driving force.

In the embodiment, there are two fourth-joint guide rails, each of which corresponds to one fourth-joint slide block, and two sides of the fourth-joint screw are respectively provided with one fourth-joint guide rail.

In the embodiment, the fifth-sixth-seventh joint module of the seven-degree-of-freedom module of the upper arm includes a fifth-shaft connector 361 connected to the fourth-shaft connector, the fifth-shaft connector 361 is connected to a shell of a fifth-shaft joint module 367, and an output shaft of the fifth-shaft joint module 367 is connected to a sixth-shaft connector 362, and the sixth-shaft connector 362 is also connected to an output shaft of a sixth-shaft joint module 363, and a shell of the sixth-shaft joint module 363 is connected to an output shaft of a seventh-shaft connector 364, and a shell of the seventh-shaft connector 364 is connected to a base of a seventh-shaft joint module 365, an output end of the seventh-shaft joint module 365 is connected to a receiving panel 366 through an end connector 368.

Where the fifth-shaft joint module, the sixth-shaft joint module and the seventh-shaft joint module all include hollow motors, harmonic reducers, band brakes and encoders, etc., which are commercially available parts and will not be described in detail.

In the embodiment, the seven-degree-of-freedom module of the lower arm includes a first-second joint module, a third joint module, a fourth-fifth joint module and a sixth-seventh joint module.

In the embodiment, the first-second joint module of the seven-degree-of-freedom module of the lower arm includes a first-shaft linear module, and a second-joint connector 324 arranged on the first-shaft linear module, and the bottom of the second-joint connector 324 is connected, through slide blocks (second-joint slide blocks 326), to guide rails (second-joint guide rails 327); and the first-shaft joint module drives the second-joint connector 324 to move along the guide rails.

The second-joint connector 324 is provided with a second-joint base 325, and the second-joint base 325 is provided with an electric cylinder, a fixed part 328 of the electric cylinder is fixed to the second-joint base, and a moving part 329 of the electric cylinder is connected to the left and right slide blocks 326, the two slide blocks are connected to the respective guide rails, and the two guide rails are vertically arranged on the second-joint base 325, and the two slide blocks are both fixedly connected to a connecting frame 330, the connecting frame 330 is connected to a third-joint connector 331, and the electric cylinder acts to drive the slide blocks to move up and down along the guide rails, and thus the connecting frame 330 connected to the slide blocks and the third-joint connector 331 on the connecting frame 330 move accordingly.

Specifically, the first-shaft linear module is the same as a first joint of the upper arm, and internally mainly includes a motor, a reducer, a screw nut pair, a bearing, etc., and a nut is used to transmit the motion of the first joint to a next part, the guide rails play a supporting role, and the moving part of the electric cylinder pushes the connecting frame to move up and down.

In the embodiment, the third joint module of the seven-degree-of-freedom module of the lower arm includes a third-joint base 338 as the third-joint connector 331, a synchronous belt transmission mechanism is installed on the third-joint base 338, a driving pulley 337 of the synchronous belt transmission mechanism is installed on an output shaft of a motor, the motor 332 is installed on the third-joint base 338 through a motor base, a driven pulley of the synchronous belt transmission mechanism is installed on a driven shaft 335, and the driven shaft 335 is mounted on the third-joint base 338 through a crossed roller bearing, the driven pulley is connected to a fourth-joint connecting plate 333, the motor rotates, so that the driven pulley rotates through a synchronous belt so as to drive the fourth-joint connecting plate 333 connected therewith to rotate.

In the embodiment, the fourth-fifth joint module of the seven-degree-of-freedom module of the lower arm includes a fourth-joint base (a lower-arm fourth-joint base 346) as the fourth-joint connecting plate 333, a guide rail (a lower-arm fourth-joint base guide rail 344) is arranged on the fourth-joint base, the guide rail is slidably connected to a slide block (a lower-arm fourth-joint base slide block 345), the slide block is provided with a lower-arm motor fixing base 343, and the motor fixing base 343 is fixedly provided with a motor (a lower-arm motor 348); the fourth-joint base is further provided with an electric cylinder fixing base 347, the electric cylinder fixing base 347 is provided with an electric cylinder, a fixed part of the electric cylinder is fixedly connected to the electric cylinder fixing base, a moving part of the electric cylinder is connected to the motor fixing base 343; the electric cylinder acts, and the moving part of the electric cylinder drives the motor to move along the guide rail 344; and a motor shaft of the motor 348 is connected to an output shaft 3410 through a coupler, and the output shaft 3410 is rotationally connected to the motor fixing base 343 through a crossed roller bearing.

In the embodiment, the sixth-seventh joint module of the seven-degree-of-freedom module of the lower arm includes a motor module fixing base 356 fixedly connected to a free end of an output shaft, a sixth-joint motor module 357 is arranged in the motor module fixing base 356, the sixth-joint motor module 357 is located in a square seventh-joint connector 353 with the bottom open, and a part, on one side of the sixth-joint motor module 357, of a connecting shaft 355 is connected to the seventh-joint connector 353 through a crossed roller bearing, and a part, on the other side of the sixth-joint motor module, of the connecting shaft is fixedly connected to the seventh-joint connector 353; an outer ring of the crossed roller bearing is connected to the seventh-joint connector 353, and an inner ring of the crossed roller bearing is connected to the connecting shaft 355; and (the sixth-joint motor module acts to drive the seventh-joint connector to act) the top of the seventh-joint connector is fixedly connected to a ball tube shell 352 internally provided with a motor reducer module 358, an outer wall of the ball tube shell is provided with a speed limiter 351, and the speed limiter 351 is connected to the motor reducer module 358.

Specifically, 358 drives 351 to rotate, and 355 denotes the connecting shaft (one side is connected to the inner ring of the crossed roller bearing, and the other side is fixedly connected to the motor module fixing base).

The objective of the present invention is to provide an all-round redundant double-arm configured angiography machine, including a seven-degree-of-freedom lower arm carrying a transmitter, a seven-degree-of-freedom upper arm carrying a receiver, a fixed table and a mobile ambulance body capable of working in the field or urban emergency environment. The central motion, the change of a detection position and the adjustment of the isocenter distance between the receiver and the transmitter are all realized through the coordination and cooperation of the upper arm and the lower arm. In the field and urban emergency environment, the wounded or patients can be rapidly treated and cured through a vehicle-mounted mode.

In the embodiment, the robot controller realizes adjustment and calibration of the robot end centering according to image data of an X-ray on the flat panel detector.

In the embodiment, the image chain system includes the ball tube, the flat panel detector, a high-voltage generator, a medical display and a workstation. Software control of the high-voltage generator, the medical display and the workstation is matched with the robot controller for application.

In the embodiment, the auxiliary system includes surgical dedicated devices such as an emergency stretcher/interventional comprehensive table, an electrocardiograph, a handheld ultrasound device, a defibrillator-monitor, an invasive blood pressure monitor and a vehicle-mounted IABP.

In the embodiment, the self-generating system is realized by a belt power takeoff driving and gearbox power takeoff parking parallel power generation technology, a belt power takeoff generator apparatus is located at an engine position, and a parking generator apparatus is located at a gearbox position.

In the embodiment, the wireless medical Internet of Things system includes a medical data acquisition terminal, a camera inside the compartment and a medical monitoring device, and wireless remote data interaction is realized after the audio and video of the physical scene in the compartment and medical device monitoring information are collected by the data acquisition terminal.

In the embodiment, the antibacterial internal environment includes laminar flow purification, ultraviolet sterilization and antibacterial material comprehensive functions.

An ambulance-type mobile catheter room for cardiovascular interventional surgery in the embodiment includes an ambulance, a self-generating system, an angiography robotic system, an auxiliary device system, a wireless medical Internet of Things system, an antibacterial internal environment, etc.

The ambulance includes a chassis and a catheter room compartment, and the chassis is combined with the self-generating system by a high-power engine and a long-axis chassis. The fixed connection between the catheter room compartment and the chassis is movable connection, and a fast fixing and dismounting structure is arranged at the junction. Four walls and a top layer of the compartment are provided with a lead protective layer. The angiography robotic system consists of upper-lower robotic arm type double robots, a controller, an image chain system and an integrated operating table. The two robots are respectively robotic arms of seven degrees of freedom, of which end portions fix a ball tube and a flat panel detector respectively, and root portions are respectively fixed to a compartment top and a compartment bottom; the image chain system includes the ball tube, the flat panel detector, a high-voltage generator, a medical display and a workstation; and the integrated operating table can have functions of an emergency stretcher and an interventional operating table. The auxiliary device system includes surgical dedicated devices such as an interventional/emergency stretcher, an electrocardiograph, a handheld ultrasound device, a defibrillator-monitor, an invasive blood pressure monitor and a vehicle-mounted IABP. A compartment body is internally equipped with auxiliary devices such as an instrument container, an apparatus container and an apparatus trolley. The compartment has functions of a laminar flow apparatus, a purification air conditioner, a fan heater, an oxygen supply system, a water supply system, video transmission, etc.

It is to be understood that the above specific description of the present invention is only used to illustrate the present invention but is not limited to the technical solutions described in the embodiments of the present invention, and those of ordinary skill in the art should understand that the present invention can still be subjected to modifications or equivalent replacements so as to achieve the same technical effect; and as long as the requirements of use are satisfied, they are all within the scope of protection of the present invention.

What is claimed is:

1. An ambulance-type mobile catheter room for cardiovascular interventional surgery, comprising an ambulance, wherein an antibacterial internal environment, a robotic angiography machine system, a wireless medical Internet of Things system, a self-generating system and an auxiliary system are provided within the ambulance; wherein the robotic angiography machine system comprises a robotic upper arm (an upper robotic arm type robot), a robotic lower arm (a lower robotic arm type robot);

wherein each of the robotic upper arm and the robotic lower arm has seven degrees of freedom and comprises a seven-degree-of-freedom module; the seven-degree-of-freedom module of the robotic upper arm comprises a first-second joint linear motion module, a third-fourth joint module, and a fifth-sixth-seventh joint module;

the first-second joint linear motion module of the seven-degree-of-freedom module of the robotic upper arm comprises a first-shaft joint linear module, and a second-shaft base arranged on the first-shaft joint linear module; a first-shaft joint linear module output end drives the second-shaft base to move, the second-shaft base is provided with second-shaft guide rails, the second-shaft guide rails are slidably connected with a second-shaft slide block, the second-shaft slide block transmits force to a screw nut pair through pulleys, two ends of a screw are supported, by thrust bearings, on the second-shaft base, and nuts are connected to the second-shaft slide block; the second-shaft guide rails comprise a first second-shaft guide rail and a second second-shaft guide rail arranged in parallel;

the third-fourth joint module of the seven-degree-of-freedom module of the robotic upper arm comprises a third joint module and a fourth joint module; the third joint module comprises a second-shaft connection block fixed to the second-shaft slide block, one side of the second-shaft connection block is connected with a curved arm type third-shaft connecting rod, a bottom of a free end of the third-shaft connecting rod is provided with a third-shaft motor, a top of the free end is provided with a third-shaft motor connector, the third-shaft motor connector is connected to the free end through a third-shaft crossed roller bearing, an outer ring of the third-shaft crossed roller bearing is connected to the free end, an inner ring of the third-shaft crossed roller bearing is connected to a third-shaft motor adapter, and the third-shaft motor is connected to the third-shaft motor adapter to transmit a motion to the third-shaft motor adapter;

the fourth joint module comprises a fourth-joint base fixedly connected to the third-shaft motor adapter, the fourth-joint base is internally equipped with a fourth-joint screw, the fourth-joint screw is installed in the fourth-joint base through a bearing seat, the fourth-joint screw is connected to a fourth-joint nut to form a screw nut kinematic pair, the fourth-joint nut is connected to a block fourth-shaft connector, the fourth-joint nut is connected to fourth-joint slide blocks, the fourth-joint slide blocks are connected to two fourth-joint guide rails, and the two fourth-joint guide rails are arranged in the fourth-joint base and are parallel with the fourth-joint screw; the fourth-joint screw transmits, by pulleys, force to the screw nut kinematic pair; each of the two fourth-joint guide rails corresponds to one fourth-joint slide block, and two sides of the fourth-joint screw are respectively provided with one fourth-joint guide rail; and the fifth-sixth-seventh joint module of the seven-degree-of-freedom module of the robotic upper arm comprises a fifth-shaft connector connected to the fourth-shaft connector, the fifth-shaft connector is connected to a shell of a fifth-shaft joint module, an output shaft of the fifth-shaft joint module is connected to a sixth-shaft connector, the sixth-shaft connector is also connected to an output shaft of a sixth-shaft joint module, a shell of the sixth-shaft joint module is connected to an output shaft of a seventh-shaft connector, a shell of the seventh-shaft connector is connected to a base of a seventh-shaft joint module, and an output end of the seventh-shaft joint module is connected to a receiving panel.

2. The ambulance-type mobile catheter room for cardiovascular interventional surgery according to claim 1, wherein the ambulance comprises a chassis and a compartment, wherein the chassis is a long-axis chassis used for assembling an engine and the self-generating system; and the compartment is movably connected to the chassis.

3. The ambulance-type mobile catheter room for cardiovascular interventional surgery according to claim 2, wherein lead plates are sandwiched between an outer wall of the compartment and an interior, and compartment windows, a compartment body and cab windows all adopt lead glass.

4. The ambulance-type mobile catheter room for cardiovascular interventional surgery according to claim 1, wherein the compartment is internally equipped with an instrument container, an apparatus container and an apparatus trolley, and the compartment is internally equipped with a laminar flow apparatus, a purification air conditioner, a fan heater, an oxygen supply system, a water supply system, and a video transmission device.

5. The ambulance-type mobile catheter room for cardiovascular interventional surgery according to claim 1, wherein the robotic angiography machine system further comprises a robot controller and an image chain system.

6. The ambulance-type mobile catheter room for cardiovascular interventional surgery according to claim 5, wherein the robot controller realizes adjustment and calibration of robot end centering according to image data of X-rays on a flat panel detector.

7. The ambulance-type mobile catheter room for cardiovascular interventional surgery according to claim 6, wherein the image chain system comprises a ball tube, the flat panel detector, a high-voltage generator, a medical display and a workstation, wherein software control of the high-voltage generator, the medical display and the workstation is matched with the robot controller for application.

8. The ambulance-type mobile catheter room for cardiovascular interventional surgery according to claim 1, wherein the auxiliary system comprises an emergency stretcher/interventional comprehensive table, an electrocardiograph, a handheld ultrasound device, a defibrillator-monitor, an invasive blood pressure monitor and a vehicle-mounted intra-aortic balloon pump (IABP);

the self-generating system comprises a generator apparatus and a gearbox; the generator apparatus comprises belt power takeoff driving, and the gearbox comprises a parking generator apparatus;

the antibacterial internal environment comprises laminar flow purification, ultraviolet sterilization lamps and an antibacterial material inner wall; and the wireless medical Internet of Things system comprises a medical data acquisition terminal, a camera inside the compartment and a medical monitoring device, wherein wireless remote data interaction is realized after audio and video of a physical scene in the compartment and medical device monitoring information are collected by the medical data acquisition terminal.

9. The ambulance-type mobile catheter room for cardiovascular interventional surgery according to claim 1, wherein the seven-degree-of-freedom module of the robotic lower arm comprises a first-second joint module, a third joint module, a fourth-fifth joint module and a sixth-seventh joint module;

the first-second joint module of the seven-degree-of-freedom module of the robotic lower arm comprises a first-shaft joint linear module, and a second-joint connector arranged on the first-shaft joint linear module, and a bottom of the second-joint connector is connected, through left and right slide blocks, to guide rails; the first-shaft joint linear module drives the second-joint connector to move along the guide rails;

the second-joint connector is provided with a second-joint base, the second-joint base is provided with an electric cylinder, a fixed part of the electric cylinder is fixed to the second-joint base, a moving part of the electric cylinder is connected to the left and right slide blocks, the left and right slide blocks are connected to respective guide rails, the two guide rails are vertically arranged on the second-joint base, the left and right slide blocks are both fixedly connected to a connecting frame, the connecting frame is connected to a third-joint connector, the electric cylinder acts to drive the left and right slide blocks to move up and down along the guide rails, and thus the connecting frame connected to the left and right slide blocks and the third-joint connector on the connecting frame move accordingly;

the third joint module of the seven-degree-of-freedom module of the robotic lower arm comprises a third-joint base as the third-joint connector, a synchronous belt transmission mechanism is installed on the third-joint base, a driving pulley of the synchronous belt transmission mechanism is installed on an output shaft of a motor, the motor is installed on the third-joint base through a motor base, a driven pulley of the synchronous belt transmission mechanism is installed on a driven shaft, the driven shaft is mounted on the third-joint base through a crossed roller bearing, the driven pulley is connected to a fourth-joint connecting plate, the motor rotates, so that the driven pulley rotates through a synchronous belt so as to drive the fourth-joint connecting plate connected therewith to rotate;

the fourth-fifth joint module of the seven-degree-of-freedom module of the robotic lower arm comprises a fourth-joint base as the fourth-joint connecting plate, a guide rail is arranged on the fourth-joint base, the guide rail is slidably connected to a slide block, the slide block is provided with a motor fixing base, and the motor fixing base is fixedly provided with a motor; the fourth-joint base is further provided with an electric cylinder fixing base, the electric cylinder fixing base is provided with an electric cylinder, a fixed part of the electric cylinder is fixedly connected to the electric cylinder fixing base, and a moving part of the electric cylinder is connected to the motor fixing base; the electric cylinder acts, and the moving part of the electric cylinder drives the motor to move along the guide rail; a motor shaft of the motor is connected to an output shaft through a coupler, and the output shaft is rotationally connected to the motor fixing base through a crossed roller bearing;

the sixth-seventh joint module of the seven-degree-of-freedom module of the robotic lower arm comprises a motor fixing base fixedly connected to a free end of the output shaft, a sixth-joint motor module is arranged in the motor fixing base, the sixth-joint motor module is located in a square seventh-joint connector with a bottom open, a part, on a first side of the sixth-joint motor module, of a connecting shaft is connected to the square seventh-joint connector through a crossed roller bearing, and a part, on a second side of the sixth-joint motor module, of the connecting shaft is fixedly connected to the square seventh-joint connector; an outer ring of the crossed roller bearing is connected to the square seventh-joint connector, and an inner ring of the crossed roller bearing is connected to the connecting shaft; and the sixth-joint motor module acts to drive the square seventh-joint connector to act; a top of the square seventh-joint connector is fixedly connected to a ball tube shell internally provided with a motor reducer module, an outer wall of the ball tube shell is provided with a speed limiter, and the speed limiter is connected to the motor reducer module.

* * * * *